United States Patent [19]

Lamberti et al.

[11] 4,025,450
[45] May 24, 1977

[54] DETERGENT COMPOSITION

[75] Inventors: Vincent Lamberti, Upper Saddle River; Mark D. Konort, Haworth, both of N.J.

[73] Assignee: Lever Brothers Company, New York, N.Y.

[22] Filed: Feb. 14, 1972

[21] Appl. No.: 226,213

Related U.S. Application Data

[63] Continuation-in-part of Ser. No. 187,115, Oct. 6, 1971, abandoned.

[52] U.S. Cl. .................. 252/89 R; 252/DIG. 11; 252/180; 252/544; 252/546; 260/535 P
[51] Int. Cl.² ............................................ C11D 1/00
[58] Field of Search ............ 252/89, 544, 180, 546, 252/DIG. 11; 260/535 P

[56] References Cited

UNITED STATES PATENTS

| | | | |
|---|---|---|---|
| 2,712,544 | 7/1955 | Bersworth | 252/DIG. 11 |
| 3,293,176 | 12/1966 | White | 210;252/58;DIG. 11 |
| 3,562,166 | 2/1971 | Nicholson | 252/541 |
| 3,725,290 | 4/1973 | Nelson et al. | 260/535 P |
| 3,896,040 | 7/1975 | Danesh | 252/89 |
| 3,954,500 | 5/1976 | Brown, Jr. | 252/89 R |

FOREIGN PATENTS OR APPLICATIONS

| | | | |
|---|---|---|---|
| 853,647 | 10/1970 | Canada | 252/DIG. 11 |
| 2,111,189 | 5/1972 | France | 252/DIG. 11 |

*Primary Examiner*—Mayer Weinblatt
*Attorney, Agent, or Firm*—Arnold Grant

[57] ABSTRACT

Disclosed herein are detergent compositions containing a water soluble organic surfactant and as a builder therefor a compound of the general formula:

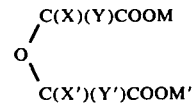

wherein X and X' are selected from the group consisting of hydrogen, alkyls having from 1 to 4 carbon atoms, alkoxys having from 1 to 4 carbon atoms, alkoxyalkyls having from 1 to 4 carbon atoms, hydroxyalkyls having from 1 to 4 carbon atoms, carboxyl in salt form (i.e., $-$ COOM), and carboxymethyloxy in salt form (i.e., $-OCH_2COOM$), with the provision that only one of X and X' can be hydrogen, alkoxy, alkoxyalkyl, hydroxyalkyl, carboxyl in salt form or carboxymethyloxy in salt form; Y and Y' are selected from the group consisting of hydrogen, alkyls having from 1 to 2 carbon atoms, and hydroxyalkyls having from 1 to 4 carbon atoms; in the cases where both X and Y' or X' and Y are hydrogen or alkyls, X' and Y or X and Y' taken together can constitute a single bond which connects the $\alpha$ and $\alpha'$ carbon atoms to form a three-membered heterocyclic ring; and M and M' are selected from the group consisting of alkali metals, ammonium and substituted ammonium cations.

8 Claims, No Drawings

DETERGENT COMPOSITION

The present application is a continuation-in-part of application Ser. No. 187,115, filed Oct. 6, 1971, now abandoned.

BACKGROUND OF THE INVENTION

1. Field of the Invention

Non-phosphorus containing builders for detergent compositions.

2. Description of the Prior Art

In recent years the problems of eutrophication which can be defined as a slow rate, natural process of enrichment of waters with nutrients, such as phosphorus and nitrogen has received much notoriety. Uncontrolled or pronounced eutrophication has been found to cause incresed algal growth and algal scums which not only are unaesthetic, odorous, distasteful and clog filters of treatment plants but also create disproportionate demands on the available oxygen in the water. It has been postulated that in several bodies of water various human activities have contributed to acceleration of the process through such factors as inordinate enrichment of natural runoff, ground water and agricultural drainage, sewage and waste effluents. It has also been suggested that the phosphorus-containing builders present in detergent compositions can be a contributing factor in eutrophication, and therefore any substitutes which do not contain phosphorus may decrease to some extent the eutrophication problem. Thus, those skilled in the art have expended a great deal of time and money to solve this problem and find suitable materials to reduce or replace the existing phosphate builders in detergent compositions. This work is still continuing since most of the builders discovered to data have been deemed unsatisfactory for a variety of reasons and are most often less efficient than the existing phosphate builders.

Salts of oxydiacetic acid, also known as diglycolic acid, are known in the art, their use as builder compounds for detergent compositions being disclosed in copending application Ser. No. 708,610, filed Feb. 27, 1968 in the name of Vincent Lamberti. While these compounds provide excellent building characteristics and are well suited for their intended use, a consistent effort has been placed on making them even more suitable and desirable as possible phosphate replacements.

In this regard the present inventors have made the unexpected discovery that when the configuration of the molecule is altered such as when certain groups are substituted onto the $\alpha$ and/or $\alpha'$ positions of the oxydiacetate molecule or when the $\alpha$ and $\alpha'$ carbon atoms are joined together to form a heterocylic ring the toxicity of the resultant compound is surprisingly and dramatically reduced. Many phosphate builder compounds, e.g., trisodium polyphosphate, have emetic properties, i.e., they cause spontaneous regurgitation if they are accidentally swallowed, and thus are considered as relatively safe in the household environment. Many of the potential phosphate replacements, unfortunately, do not possess this characteristic so that the toxicity of the compound becomes an exceedingly important factor in the choice of a possible replacement—the assumption having to be made that small children are prone to ingest anything within their reach, including detergent compositions. In point of fact there are several thousand reported cases a year of household cleanser ingestions. Thus, if a particular compound can be found which demonstrates both good detergency building characteristics and which can be classified as non-toxic, a substantial step forward will have been made toward the goal of an acceptable non-phosphorus containing builder.

SUMMARY OF THE INVENTION

The present inventors have found that compounds according to the general formula:

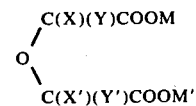

wherein X and X' are selected from the group consisting of hydrogen, alkyls having from 1 to 4 carbon atoms, alkoxys having from 1 to 4 carbon atoms, alkoxyalkyls having from 1 to 4 carbon atoms, hydroxyalkyls having from 1 to 4 carbon atoms, carboxyl in salt form (i.e.,-COOM), and carboxymethyloxy in salt form (i.e., —OCH$_2$— COOM) with the provision that only one of X and X' can be hydrogen, alkoxy, alkoxyalkyl, hydroxyalkyl, carboxyl or carboxymethyloxy; Y and Y' are selected from the group consisting of hydrogen, alkyls having from 1 to 2 carbon atoms, and hydroxyalkyls having from 1 to 4 carbon atoms; further provided that in the cases where both X and Y' or X' and Y are hydrogen or alkyls, X' and Y or X and Y' taken together can constitute a single bond which connects the $\alpha$ and $\alpha'$ carbon atoms to form a three-membered heterocylic ring; and, M and M' are selected from the group consisting of alkali metals, ammonium and substituted ammonium cations, have both good detergent building properties and can be classified as non-toxic. The preferred compounds are the $\alpha$-methyl and $\alpha,\alpha'$-dimethyl, the $\alpha$-carboxymethyloxy, the $\alpha$-methoxy, $\alpha$-ethoxy, the ($\alpha$-methoxy-$\alpha'$hydroxymethyl), the ($\alpha$-ethoxy-$\alpha'$-hydroxymethyl) substituted oxydiacetate salts, and the epoxysuccinate salts. Preferred cations are the alkali metals, with sodium being the most preferred. The ($\alpha,\alpha'$-dimethyl)oxydiacetates are also known as dilactates and, accordingly the sodium salt would be called disodium dilactate.

DETAIL DESCRIPTION OF THE INVENTION

The compositions of the invention necessarily include both a synthetic builder and a water-soluble organic detergent compound. Detergent compounds useful in the present invention are the anionic (soap and nonsoap), zwitterionic and ampholytic detergent compounds. The chemical nature of these detergent compounds is not an essential feature of the present invention. Moreover, such detergent compounds are well known to those skilled in the detergent art and the patent and printed literature are replete with disclosures of such compounds. Typical of such literature are "Surface Active Agents" by Schwartz and Perry and "Surface Active Agents and Detergents" by Schwartz, Perry and Berch, both Interscience Publishers, N.Y., N.Y., the disclosures of which are incorporated by reference herein.

The phosphorus-free synthetic builders for the detergent compositions according to the present invention are $\alpha$ and/or $\alpha'$-mono-, di- or trisubstituted oxydiacetates and $\alpha$ and/or $\alpha'$ substituted and unsubstituted heterocyclic (i.e., α–α'-linked) oxydiacetates which can be represented by the general formula:

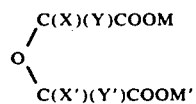

wherein X and X' are selected from the group consisting of hydrogen, alkyls having from 1 to 4 carbon atoms, alkoxys having from 1 to 4 carbon atoms, alkoxyalkyls having from 1 to 4 carbon atoms, hydroxyalkyls having from 1 to 4 carbon atoms, carboxyl in salt form (i.e.,—COOM), and carboxymethyloxy in salt form (i.e., —OCH$_2$COOM), with the provision that X and X' cannot both be hydrogen, or both be alkoxy or both be alkoxyalkyl, or both be carboxyl, or both be carboxymethyloxy; Y and Y' are selected from the group consisting of hydrogen, alkyls having from 1 to 2 carbon atoms, and hydroxyalkyls having from 1 to 4 carbon atoms; further provided that in the cases where both X and Y' or X' and Y are hydrogen or alkyls having from 1 to 4 carbon atoms, X' and Y or X and Y' taken together can constitute a single bond which connects the α and α' carbon atoms to form a three-membered heterocylic ring; and, M and M' are selected from the group consisting of alkali metals, ammonium and substituted ammonium cations. The α and α' substituents in the case of di- or tri-substituted compounds can either be the same or different, as long as they are chosen from the above group. As stated, however, X and X' can only be the same substituent in the case of alkyls. The preferred compounds are the α-methyl and α,α'-dimethyl, the α-carboxymethyloxy, the α-methoxy, α-ethoxy, the (α-methoxy-α'-hydroxymethyl), the (α-ethoxy-α'-hydroxymethyl) substituted oxydiacetate salts and the epoxy-succinate salts. Preferred cations are the alkali metals, lithium, sodium, potassium, with sodium being the most preferred.

Examples of such α and/or α' groups for alkyl substituents would include methyl, ethyl, n-propyl, isopropyl, n-butyl, sec-butyl and isobutyl. Preferred examples of alkoxy substituents would include, but are not limited to, methoxy, ethoxy, n-propoxy, isopropoxy, n-butoxy, sec-butoxy and isobutoxy. Preferred examples of alkoxyalkyls would include, but are not limited to, methoxymethyl, ethoxymethyl, isopropoxymethyl, methoxyethyl, and ethoxyethyl. Preferred examples of hydroxyalkyl substituents are hydroxymethyl, hydroxyethyl, hydroxypropyl, hydroxyisopropyl, hydroxybutyl, sec-hydroxybutyl and hydroxyisobutyl.

As stated, in the case where X' and Y or X and Y' constitute a single bond to form the compound

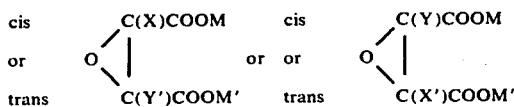

the X and/or Y' or X' and/or Y positions may be hydrogen or alkyl as previously defined.

Thus, hereinafter the term "α–α' linked heterocylic oxydiacetate salts" is intended to include both the cis and trans forms of these compounds without further substituents in the remaining X or X' or Y or Y' positions (i.e., these positions are occupied by hydrogen atoms) and both the cis and trans forms of these compounds where there are alkyl or both hydrogen and alkyl substituents according to the above defined group of these positions. That is, the term "epoxysuccinate" as used in the present specification and claims is intended to include unsubstituted as well as mono- or di-substituted epoxysuccinates wherein the substituents are selected from the group consisting of alkyls having from 1 to 4 carbon atoms.

Typical α and/or α' substituted and α–α' linked heterocyclic oxydiacetate salts suitable as the builder for the detergent compositions according to the present invention are the normal sodium, potassium, mixed sodium potassium, lithium, ammonium, methylammonium, (tertramethyl)ammonium, the normal monoethanolamine, diethanolamine and triethanolamine salts, the normal monoisopropanolamine salts, the normal diisopropanolamine salts, the normal morpholine salts and the like. These αand/or α ' substituted and α–α' linked heterocyclic oxydiacetate or diglycolate salts, in common with the known commercial builders, are sequestrants and chelators for the calcium, magnesium and other metal ions present in hard water.

The weight ratio of α and/or α' substituted and/or α–α' linked heterocyclic oxydiacetate builders, it being understood that these salts can be used separately or in conjunction with each other, to a detergent compound when used in laundering compositions ranges generally from about 1:20 to about 20:1. When the novel builders are used in mechanical dishwashing compositions, the ratio of builder to detergent compound is from about 10:1 to about 50:1. Additionally, the α and/or α' substituted and/or α–α' linked heterocyclic oxydiacetate or diglycolate builders can be used either as the sole builder or in combination with each other as joint builders, or, where desired, either or both together can be used in conjunction with other well known builders, examples of which include tetrasodium and tetrapotassium pyrophosphate, pentasodium and pentapotassium tripolyphosphate, trisodium and tripotassium nitrilotriacetate, disodium oxydiacetate, trisodium carboxymethyloxysuccinate, tetrasodium tetrahydrofurantetracarboxylate, oxidized starches, and the like. Other materials which may be present in the detergent compositions of the invention in minor amounts, are those conventionally present therein. Typical examples thereof include the well known soil-suspending agents, hydrotropes, corrosion inhibitors, dyes, bleaches, perfumes, fillers, optical brighteners, enzymes, suds boosters, suds depressants, germicides, anti-tarnishing agents, cationic detergents and the like. The balance of the detergent compositions is water.

When using the detergent compositions of the invention to wash clothes, the wash solutions should have a pH from about 7 to 12 and preferably from about 9 to 11. Therefore, the presence of an alkaline buffer in the detergent composition is usually desirable particularly when the soil to be removed from the clothes has a high content of acidic components. Suitable buffers include any of the common organic and/or inorganic buffers as monoethanolamine, triethanolamine, sodium and potassium silicates, sodium and potassium carbonates and the like.

It was also discovered that, rather surprisingly, when higher than normal levels of anionic, nonionic, ampholytic or zwitterionic surfactants are used with the substituted oxydiacetate salts and the epoxysuccinate salts of the present invention, the detergency of the formulations is significantly enhanced. The detergent formulations should contain surfactant levels of about 10 to about 45% with the preferred level being about 25 to 35% by weight and α and/or α' substituted and/or α–α' linked heterocyclic oxydiacetate salt levels of about 25% to about 75% by weight in the cases when the surfactants are anionic, ampholytic or zwitterionic. When the surfactant is a nonionic the level of said nonionic in the formulation is from about 5 to about 30% by weight and αand/or α' substituted and/or α–α' linked heterocyclic oxydiacetate salts is from about 25 to about 85% by weight. Mixtures of anionic and nonionic surfactants have been found to be particularly advantageous with the builder salts of the present invention.

It was also found that exceptionally good results are obtained when the surfactant is selected from an anionic or zwitterionic class and particularly when the surfactant is linear secondary alkyl ($C_{10}$–$C_{15}$) benzenesulfonate salt or alpha-olefin sulfonate salts having a chain length from about $C_{12}$ to about $C_{18}$.

The detergent compositions of the present invention may be in any of the usual physical forms for such compositions, such as powders, beads, flakes, bars, tablets, liquids, pastes, and the like. The compositions are prepared and utilized in the conventional manner.

As stated above, a particular advantage of the builders of the present invention over the salts of unsubstituted oxydiacetic acid, is their lower toxicity. For example, using Webster mice, the acute oral toxicity data, ($LD_{50}$), i.e., the dosage in grams per kilogram of body weight which is lethal for 50% of the mice, for two of the preferred embodiments compared to disodium oxydiacetate are as follows:

TABLE I

| Sample | $LD_{50}$ | Remarks |
|---|---|---|
| disodium oxydiacetate | 2.85 | slightly toxic |
| disodium (α-methyl)-oxydiacetate | > 5 | non-toxic |
| disodium (α, α'-dimethyl)-oxydiacetate | > 5 | non-toxic |

Similar results obtain with the other embodiments of the present invention. Absence of toxicity, as previously brought out, is an extremely important factor, in selection of a builder compound, since the emetic properties possessed by the usual phosphate builders will no longer be present in the detergent compositions. That is, the composition, if accidentally ingested, will more than likely remain in the stomach unless removed by artificial means, so that toxicity may well provide to be a deciding factor in selection of potential phosphate replacements. As can be seen from Table I, the novel compounds of the present invention are classified as nontoxic.

It is of course understood and appreciated that many of the compounds of the present invention form hydrates in the isolatable form. Thus, when in the course of the instant specification and claims a compound is named it is intended to include both the hydrate and anhydrous forms.

The disodium (α-methyl)oxydiacetate and disodium (α,α'-dimethyl)oxydiacetate builder salts can be prepared by the method taught by Arlette Solladie-Cavallo and Pierre Vieles in Bull. Soc. Chim. de France 1967, (2) starting at page 517, the disclosures of which are incorporated herein by reference. Similarly the other mono- and dialkyl substituted acids according to the present invention may be prepared and neutralized by the appropriate base to the salts by the same method taught therein, i.e., by utilizing the appropriate α-hydroxy-carboxylic ester and α-halocarboxylic ester.

The following examples illustrate without limiting the invention herein the preparation of alkyl, alkoxy, carboxy, carboxymethyloxy, alkoxyalkyl and hydroxyalkyl substituted salts found suitable as builder salts.

EXAMPLES 1–2

Preparation of Disodium (α-methoxy)oxydiacetate and Trisodium (α-Carboxymethyloxy)oxydiacetate 46 g. (2.0 moles) of sodium metal is slowly dissolved in 350 ml. of anhydrous methanol. Methyl glycolate, 200 g. (2.22 moles), is then added to the methoxide solution. After stirring at room temperature for 15 minutes, methanol is removed in vacuo. Next, 142 g. (1.0 mole) of methyl dichloroacetate is added to the residue and the mixture heated to reflux. After the resulting exothermic reaction subsides, the reaction mixture is refluxed for 12 hours. The mixture is then filtered and the filtrate, concentrated. Vacuum distillation of the residue gives (1) 24.2 g. of dimethyl (α-methoxy)oxydiacetate b.p. 85°–90° C (0.18 mm); NMR spectrum ($CDCl_3$ with internal tetramethylsilane standard), singlet at 5.02δ (1H), singlets at 3,80δ, 3.75δ and 3.47δ (3H each) and (2) 19.1 g. of trimethyl (α-carboxymethyloxy)oxydiacetate, b.p. 138°–140° C (0.60 mm); NMR spectrum ($CCl_4$ with external tetramethylsilane standard): singlet at 5.0δ (1H), singlet at 4.19δ (4H), singlets at 3.65 and 3.59δ (total of 9H).

24.2 g. (0.126 mole) of dimethyl (α-methoxy)oxydiacetate and 10.1 g. (0.25 mole) of sodium hydroxide in 150 ml water are heated on the steam bath for 2 hours. The solution is then added to about 3 liters of ethanol. The resulting precipitate is filtered and dried to give disodium (α-methoxy)oxydiacetate.

Alternatively, strontium (α-methoxy)oxydiacetate, prepared according to the method of Jackson and Hudson, J. Am. Chem. Soc. 59, 994 (1937), is reacted with an equivalent amount of aqueous sodium carbonate, filtered to remove the precipitated strontium carbonate and the filtrate evaporated to give the disodium (α-methoxy)oxydiacetate.

19.1 g. (0.076 mole) of trimethyl (α-carboxymethyloxy)oxydiacetate and 9.5 g. (0.24 mole) of sodium hydroxide in 150 ml. water are heated on a steam bath for 2 hours. The solution is then added to about 3 liters of ethanol. The resulting precipitate is filtered and dried to give trisodium (α-carboxymethyloxy) oxydiacetate.

EXAMPLE 3

Preparation of Disodium (α-methoxy-α'-methyl)oxydiacetate

α-Methyl galactomethylpyranoside is oxidized, according to the method described by Maclay, Hahn and Hudson in J. Am. Chem. Soc. 61 1660–6 (1939), to yield (α-methoxy-α'-methyl)oxydiacetaldehyde which is subsequently converted to the strontium salt of (α-methoxy-α'methyl)oxydiacetic acid. The strontium salt is treated with an equivalent amount of aqueous sodium carbonate, filtered to remove the precipitated strontium carbonate and the filtrate then evaporated to give the desired disodium (α-methoxy-α'-methyl)oxydiacetate.

EXAMPLE 4

Preparation of Disodium (α-methoxy-α'-hydroxymethyl)oxydiacetate

This compound may be prepared with the aid of the methods outlined by Jackson and Hudson, J. Am. Chem. Soc. 59, 994 (1937), Boothroyd, Brown, Thorn and Neish, Can. J. Biochem. and Physiol. 33, 62–8 (1955) and Goldstein, Hamilton and Smith, J. Am. Chem. Soc. 79, 1190 (1957). That is, periodic acid oxidation of methyl α-glucopyranoside to (α-methoxy-α'-hydroxymethyl)oxydiacetaldehyde which is subsequently oxidized and isolated as the strontium salt of (α-methoxy-α'-hydroxymethyl)oxydiacetic acid. The strontium salt is treated with an equivalent amount of aqueous sodium carbonate, filtered to remove the precipitated strontium carbonate and the filtrate evaporated to give the disodium (α-methoxy-α'-hydroxymethyl)oxydiacetate.

EXAMPLE 5

Preparation of Disodium (α-methoxy-α'-methoxymethyl)oxydiacetate

Disodium (α-methoxy-α'-methoxymethyl)oxydiacetate is obtained by alcoholic sodium hydroxide hydrolysis of the dimethyl ester as described for the methyl substituted analogs by Solladie-Cavallo and P. Vieles, Bull. Soc. Chim. de France 1967 (2) p. 517. The dimethyl (α-methoxy-α'-methoxymethyl)oxydiacetate is prepared from the strontium salt of (α-methoxy-α'-hydroxymethyl)oxydiacetate (described above) by acidifying, converting to the silver salt with silver oxide and treating with methyl iodide as described by Irwin J. Goldstein, J. K. Hamilton and F. Smith J. Am. Chem. Soc 79, 1190 (1957).

EXAMPLE 6

Preparation of Disodium (α-hydroxymethyl)-oxydiacetate

Disodium (α-hydroxymethyl)oxydiacetate is prepared by a five step synthesis involving a reaction sequence which can be summarized as follows:

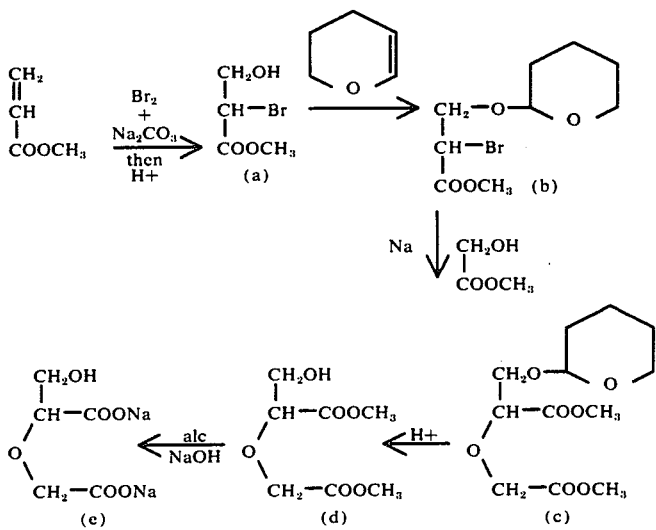

Compound (a), methyl 2-bromo-3-hydroxypropionate is prepared from methyl acrylate according to Albert M. Mattocks and Walter H. Hartung, J. Biol. Chem, 165, 501 (1946). The primary hydroxyl group is protected by treatment with dihydropyran yielding compound (b) according to G. F. Woods and D. N. Kramer in J. Am. Chem. Soc. 69, 2246 (1947). Compound (b) is then reacted with methyl glycolate in the presence of sodium as reported by A. Solladie-Cavallo and P. Vieles, Bull. Soc. Chim. de France 1967 (2), p. 517 to yield compound (c). Compound (c) is converted to compound (d) by regenerating the hydroxyl group by acid hydrolysis. Alcoholic sodium hydroxide saponification yields compound (e), i.e., disodium (α-hydroxymethyl)oxydiacetate. The hydrolysis of substituted oxydiacetate esters is described by A. Solladie-Cavallo and P. Vieles, Bull. Soc. Chim. de France 1967 (2) p. 517. Alternatively, strontium (α-hydroxymethyl)oxydiacetate, prepared according to Carson and Maclay [J. Am. Chem. Soc. 67, page 1808 (1945)], is reacted with an equivalent amount of aqueous sodium carbonate, filtered to remove the precipitated strontium carbonate and the filtrate evaporated to give compound (e).

EXAMPLE 7

Preparation of Disodium (α-methoxymethyl)-oxydiacetate

Disodium (α-methoxymethyl)oxydiacetate is prepared by treating dimethyl (α-hydroxymethyl)oxydiacetate (described as compound (d) in Example 6) with methyl iodide. The resulting dimethyl ester is then saponfied with alcoholic sodium hydroxide. An alternate route can be illustrated as follows:

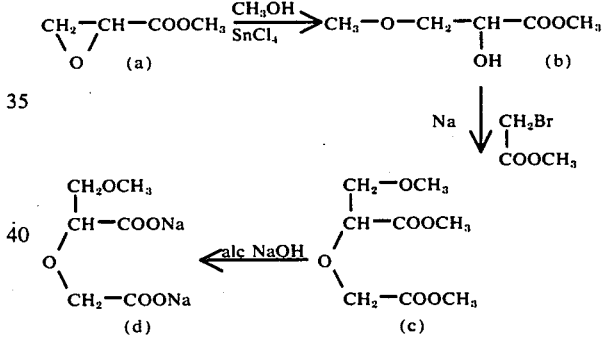

Compound (a), methyl glycidate described by R. W. White and W. D. Emmons in Tetrahedron (1962) 17, 31, is converted to methyl α-hydroxy-β-methoxypropionate (b) by refluxing with methanol in the presence of 1% stannic chloride (basis amount of methyl glycidate.) Compound (b) is then reacted with sodium and methyl bromoacetate according to the procedure described by A. Solladie-Cavallo and P. Vieles in Bull. Soc. Chim. de France 1967 (2), p. 517. The same reference describes the conversion of this type of ester (analogous to compound (c)) to the disodium (α-methoxymethyl)oxydiacetate (d).

EXAMPLE 8

Preparation of Epoxysuccinates

Salts of epoxysuccinic acid are readily prepared by first preparing the desired epoxysuccinic acid (cis or trans) according to the methods described by Gawron et al. J. Amer. Chem. Soc. 80, 5856 (1958) and then neutralizing with the required amount of the appropriate alkali metal, ammonium or substituted ammonium hydroxide. Alternatively, the disodium salt of epoxysuccinic acid may be prepared using the method of Payne and Williams, J. Org. Chem. 24 54 (1959).

EXAMPLE 9

Cis and Trans Disodium Epoxysuccinates

These compounds are prepared according to the methods of Gawron et al., J. Am. Chem. Soc. 80 5856 (1958).

EXAMPLE 10

Disodium (α-Methoxy-α'-Hydroxy-methyl)oxydiacetate

Methyl α-D-glucopyranoside, 10.0 g., is dissolved in 200 ml of water. Then, 14.4 g. of 50% sodium hydroxide solution is added followed by a mixture of 54.3 g. of silver oxide and 12.7 g. of powdered silver. The reactant mixture is stirred vigorously and the ensuing exothermic reaction allowed to raise the temperature to 35°–40° C. The reaction mixture is then maintained at 40° C for 2 hours after which it is cooled to room temperature and neutralized to pH 8.5 with concentrated hydrochloric acid. After filtering off the Ag/AgCl phase, the filtrate is concentrated in vacuo to about 75 ml. and then mixed with 800 ml. of 3A ethyl alcohol. The resulting crystalline precipitate is then filtered and dried in vacuo over phosphorus pentoxide to give 13.3 g. of product containing 83.0% disodium (α-methoxy-α'hydroxymethyl)oxydiacetate as determined by NMR analysis ($D_2O$) using an internal standard of potassium biphthalate. The product may be further purified by recrystallization from ethanol-water.

EXAMPLE 11

Disodium (α-Methoxy-α-Hydroxymethyl)-oxydiacetate

Fructose is first converted into Methyl β-fructopyranoside which is then oxidized with silver oxide/silver according to the procedure given in Example 10 above for the preparation of disodium (α-methoxy-α'-hydroxymethyl)oxydiacetate.

EXAMPLE 12

Trisodium (α-Methoxy-α'Carboxy)-oxydiacetate

A mixture of Methyl β-glucuronoside and its methyl ester is first prepared by heating for 2 hours at 100° C (autoclave) with stirring polyglucuronic acid (isolatable from cereal straws and grains) with five parts of methanol containing 10% by weight of 95% sulfuric acid. The mixture is discharged from the autoclave, neutralized with a methanolic solution of sodium methylate and evaporated to remove the methanol. The residue is then oxidized with a mixture of silver oxide/silver using the oxidation procedure described in Example 10 above and using a mole ratio of $Ag_2O$/Ag/NaOH/ starting polyglucuronic acid of 3.0/1.5/3.0/1.0. The isolated product is recrystallized from ethanol-water.

EXAMPLE 13

Trisodium (α-Carboxy)oxydiacetate

This product is readily obtained via the Williamson ether synthesis using the sodium alkoxide of methyl glycolate and dimethyl bromomalonate in ether solution. The resulting ester is isolated by distillation and hydrolyzed with a slightly excess of 15% sodium hydroxide. The pH of the solution is adjusted to 8.6 with a cation exchange resin, and after filtration, the filtrate is evaporated to dryness to yield the title compound.

EXAMPLE 14

Disodium[α-ethoxy-α,α'-bis(hydroxymethyl)]oxydiacetate

Ethyl β-D-fructofuranoside is oxidized according to the procedure of Example 10 above for the preparation of disodium (α-methoxy-α'-hydroxymethyl)oxydiacetate except that the mole ratio of $Ag_2O$/Ag/NaOH/fructo-furanoside is 3.0/1.5/2.5/1.0. The product is recrystallized from ethanol-water.

EXAMPLES 15–62

The detergent formulations set forth in Table II–VIII below were prepared by blending together the recited components and were then tested for detergency or cleansing ability in the Terg-o-Tometer Test wherein the washing conditions were as follows: VCD (vacuum cleaner dust) soil cloth; 120° F; 180 ppm water (2/1 Ca++/Mg++); 0.15% concentration of total formulation in washing solution; pH 10. The following abbreviations have been used therein: LAS is sodium linear secondary alkyl ($C_{10}$–$C_{15}$) benzenesulfonate, Tergitol 15-S-7 is an adduct of 7 moles of ethylene oxide with 1 mole of a $C_{11}$–$C_{15}$ random linear secondary alcohol derived from $C_{11}$–$C_{15}$ normal paraffins, $C_{14}$–$C_{16}$HAMT is an ampholytic surfactant which is sodium hydroxyalkyl ($C_{14}$–$C_{16}$) N-methyltaurate, Sulfobetaine DCH is a zwitterionic surfactant which is cocodimethylsulfopropylbetaine, RU silicate solids is a sodium silicate having a $SiO_2$: $Na_2O$ ratio of 2.4:1. The detergency of the formulation is expressed in "Detergency Units" (DU's) which is obtained by subtracting the initial reflectance of the soil cloth from the final reflectance of the washed cloth (the average of two runs). The reflectances are measured with a Gardner Automatic Color Difference Meter.

TABLE II

| Component | \multicolumn{8}{c}{Example Formulation (%)} | | | | | | | |
|---|---|---|---|---|---|---|---|---|
| | 15 | 16 | 17 | 18 | 19 | 20 | 21 | 22 |
| Disodium (α-Methyl)oxydiacetate | 50 | — | 50 | — | 50 | — | 50 | — |
| Sodium tripolyphosphate | — | 50 | — | 50 | — | 50 | — | 50 |
| Sodium α-$C_{15-18}$ olefin sulfonate | 18 | 18 | — | — | — | — | — | — |
| Tergitol 15:S:7 | — | — | 10 | 10 | — | — | — | — |
| $C_{14-16}$ HAMT | — | — | — | — | 18 | 18 | — | — |
| Sulfobetaine DCH | — | — | — | — | — | — | 18 | 18 |
| RU Silicate Solids | 10 | 10 | 10 | 10 | 10 | 10 | 10 | 10 |
| Water | \multicolumn{8}{c}{balance} | | | | | | | |
| Detergency (DU's) | 24.0 | 28.6 | 19.3 | 25.9 | 22.7 | 27.0 | 25.3 | 31.2 |
| % Efficiency relative to control (i.e. 15 vs. 16, 17 vs. 18, 19 vs. 20 and 21 vs. 22) | 84 | | 75 | | 84 | | 81 | |

TABLE III

| Component | Example Formulation (%) | | | |
|---|---|---|---|---|
| | 23 | 24 | 25 | 26 |
| Disodium (α-Methyl) oxydiacetate | 50 | — | — | — |
| Disodium (α, α'-Dimethyl) oxydiacetate | — | 50 | — | — |
| Disodium Oxydiacetate | — | — | 50 | — |
| Sodium Tripolyphosphate | — | — | — | 50 |
| LAS | 18 | 18 | 18 | 18 |
| RU Silicate Solids | 10 | 10 | 10 | 10 |
| Water | \multicolumn{4}{c}{balance} | | | |
| Detergency (DU's): | 28.1 | 24.8 | 27.8 | 31.1 |
| % Efficiency relative to control formulation 26 | 90 | 80 | 89 | |

TABLE IV

| Component | Example Formulation (%) | | | |
|---|---|---|---|---|
| | 27 | 28 | 29 | 30 |
| LAS | 18 | — | 18 | 18 |
| Disodium epoxysuccinate | — | 50 | 50 | — |
| STPP | — | — | — | 50 |
| RU Silicate Solids | 6 | 6 | 6 | 6 |
| Water | \multicolumn{4}{c}{bal.} | | | |
| Detergency (DU's): | 4.5 | 2.7 | 18.5 | 25.6 |

Comparison of formulation 29 vs. 27 and 28 shows synergistic building action of epoxysuccinate with LAS. The relatively low detergency units in example 28, which was in contrast to other data reproduced herein, see Table VII, was found to be due to the presence of an impurity in the disodium epoxysucciniate. However, even with the impurity the building action and synergism is clearly demonstrated.

TABLE V

| Component | Example Formulation (%) | | | |
|---|---|---|---|---|
| | 31 | 32 | 33 | 34 |
| Disodium (α-Methoxy) oxydiacetate | 50 | — | — | — |
| Trisodium (α-carboxymethyloxy)oxydiacetate | — | 50 | — | — |
| Disodium Oxydiacetate | — | — | 50 | — |
| Sodium Tripolyphosphate | — | — | — | 50 |
| LAS | 18 | 18 | 18 | 18 |
| RU Silicate Solids | 10 | 10 | 10 | 10 |
| Water | \multicolumn{4}{c}{balance} | | | |
| Detergency (DU's): | 28.2 | 29.4 | 28.9 | 31.3 |
| % Efficiency relative to control formulation 34 | 90 | 94 | 92 | |

Quite similar results are to be found with the other alkyls, alkoxys, alkoxyalkyls and hydroxyalkyl substituents recited above and falling within the definition of the present invention.

TABLE VI

| Component | Example Formulation (%) | |
|---|---|---|
| | 35 | 36 |
| LAS | 18 | 18 |
| Disodium (α-Methoxy-α'hydroxymethyl)oxydiacetate | 50 | — |
| STPP | — | 50 |
| RU Silicate Solids | 10 | 10 |
| Water | \multicolumn{2}{c}{balance} | |
| Detergency (DU's) | 25.8 | 30.0 |

TABLE VII

| Component | Formulation (%) | | | | | | | | | | | |
|---|---|---|---|---|---|---|---|---|---|---|---|---|
| | 37 | 38 | 39 | 40 | 41 | 42 | 43 | 44 | 45 | 46 | 47 | 48 |
| LAS | 18 | 18 | 18 | 18 | 18 | 18 | 27 | 27 | 27 | 18 | 18 | 18 |
| Disodium cis-Epoxysuccinate | 50 | — | — | 50 | — | — | 50 | — | — | 50 | — | — |
| Disodium trans-Epoxysuccinate | — | 50 | — | — | — | — | — | — | 50 | — | 50 | — |
| Disodium Oxydiacetate | — | — | — | — | 50 | — | — | 50 | — | — | — | 50 |
| STPP | — | — | 50 | — | — | 50 | — | — | — | 50 | — | — |
| RU Silicate Solids | 10 | 10 | 10 | 10 | 10 | 10 | 10 | 10 | 10 | 10 | 10 | 10 |
| Water | bal. | bal. | bal. | bal. | bal. | bal. | bal. | bal. | bal. | bal. | bal. | bal. |
| Formulation Concentration (%) | 0.15 | 0.15 | 0.15 | 0.1 | 0.1 | 0.1 | 0.1 | 0.1 | 0.1 | 0.2 | 0.2 | 0.2 |
| Detergency (Du's) | 29.3 | 29.1 | 26.6 | 27.3 | 31.4 | 28.8 | 28.5 | 28.5 | 29.0 | 31.6 | 31.8 | 33.1 |

As can be seen from the data in Table VII, both the cis- and trans-epoxysuccinates are detergent builders for linear $C_{10}$–$C_{15}$ alkylbenzene sulfonate (LAS) being equal to each other and to disodium oxydiacetate.

TABLE VIII

| Component | Formulation (%) | | | | | | | |
|---|---|---|---|---|---|---|---|---|
| | 49 | 50 | 51 | 52 | 53 | 54 | 55 | 56 |
| Sodium α-$C_{15-18}$ olefin | 18 | 18 | — | — | — | — | — | — |
| Tergitol 15-S-7 | — | — | 10 | 10 | — | — | — | — |
| $C_{14-16}$ HAMT | — | — | — | — | 18 | 18 | — | — |
| Sulfobetaine DCH | — | — | — | — | — | — | 18 | 18 |
| Disodium cis-epoxysuccinate | 50 | — | 50 | — | 50 | — | 50 | — |
| STPP | — | 50 | — | 50 | — | 50 | — | 50 |
| RU Silicate Solids | 10 | 10 | 10 | 10 | 10 | 10 | 10 | 10 |
| Water | balance | | | | | | | |
| Detergency (DU's) | 23.4 | 25.8 | 24.3 | 29.2 | 23.7 | 25.2 | 26.5 | 28.3 |

EXAMPLE 57

A machine dishwashing composition is prepared with the following materials:

| | |
|---|---|
| Disodium (α-methyl)oxydiacetate | 43.0% |
| Chlorinated trisodium phosphate | 21.0% |
| Sodium Silicate Solids (3.22 SiO$_2$/Na$_2$O ratio) | 14.0% |
| Sodium Silicate Solids (2.4 SiO$_2$/Na$_2$O ratio) | 12.0% |
| Pluronic L62 (A nonionic surfactant sold by Wyandotte Chemical Corporation and which is an ethylene oxide condensate of a polyoxypropylene glycol) | 2.5% |
| Sodium Sulfate | 4.7% |
| Water | 2.8% |

A similar dishwashing composition, utilizing a compound according to the present invention, but without chlorinated trisodium phosphate can be prepared as follows:

EXAMPLE 58

Dishwashing composition containing Disodium (α-methyl)oxydiacetate

| | |
|---|---|
| Disodium (α-methyl)oxydiacetate | 43.0% |
| Potassium Dichlorocyanurate | 1.5% |
| Sodium Silicate Solids (3.22 SiO$_2$/Na$_2$O ratio) | 15.0% |
| Pluronic L62 (a nonionic surfactant sold by Wyandotte Chemical Corporation and which is an ethylene oxide condensate of a polyoxypropylene glycol) | 2.5% |
| Sodium carbonate | 20.0% |
| Sodium sulfate (balance) | 18.0% |

The above formulas have acceptable dishwashing properties which are quite similar to those products containing sodium tripolyphosphate.

It will be appreciated that various changes and modifications, in addition to those set forth above, may be made by those skilled in the art without departing from the essence of the present invention and that accordingly the invention is to be limited only within the scope of the appended claims.

We claim:

1. A detergent composition consisting essentialy of a water-soluble organic detergent compound selected from the group consisting of anionic, nonionic, zuritterionic and ampholytic detergent compounds and as a detergent builder a compound represented by the formula:

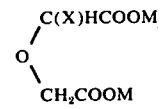

wherein X is an alkyl having from 1 to 4 carbon atoms and M is selected from the group consisting of alkali metals, ammonium, methylammonium, tetramethylammonium, normal monoethanolamine, diethanolamine, triethanolamine salts, normal monoisopropanolamine salts, normal diisopropanolamine salts and normal morpholine salts, the weight ratio of detergent builder to detergent compound ranging from about 1:20 to about 50:1.

2. A detergent composition as defined in claim 1 wherein the detergent builder is an (α-methyl)-oxydiacetate salt.

3. A detergent composition as defined in claim 1 wherein M and M' are sodium.

4. A detergent composition as defined in claim 1 wherein M and M' are lithium.

5. A detergent composition as defined in claim 1 wherein M and M' are potassium.

6. A detergent composition as defined in claim 1 wherein M and M' are ammonium.

7. A detergent composition as defined in claim 1 wherein M is sodium and M' is potassium.

8. A detergent composition as defined in claim 1 wherein the weight ratio of the detergent builder to the detergent compound ranges from about 1:20 to about 20:1.

* * * * *